(12) United States Patent
Watanabe et al.

(10) Patent No.: US 9,586,887 B2
(45) Date of Patent: Mar. 7, 2017

(54) METHOD FOR PRODUCING ESTER COMPOUND

(71) Applicant: JX NIPPON OIL & ENERGY CORPORATION, Chiyoda-ku, Tokyo (JP)

(72) Inventors: Daisuke Watanabe, Tokyo (JP); Masaki Noguchi, Tokyo (JP); Akira Shiibashi, Tokyo (JP); Shinichi Komatsu, Tokyo (JP); Takaya Matsumoto, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 14/889,978

(22) PCT Filed: Apr. 18, 2014

(86) PCT No.: PCT/JP2014/061056
§ 371 (c)(1),
(2) Date: Nov. 9, 2015

(87) PCT Pub. No.: WO2014/181664
PCT Pub. Date: Nov. 13, 2014

(65) Prior Publication Data
US 2016/0102044 A1 Apr. 14, 2016

(30) Foreign Application Priority Data
May 8, 2013 (JP) .................. 2013-098564

(51) Int. Cl.
*C07C 67/36* (2006.01)
*C07C 67/475* (2006.01)
*C07C 67/38* (2006.01)
*B01J 31/18* (2006.01)

(52) U.S. Cl.
CPC ......... *C07C 67/475* (2013.01); *B01J 31/1815* (2013.01); *C07C 67/38* (2013.01); *B01J 2231/49* (2013.01); *B01J 2231/70* (2013.01); *B01J 2531/824* (2013.01); *C07C 2103/94* (2013.01)

(58) Field of Classification Search
CPC ... C07C 67/38; C07C 69/757; C07C 2103/94; C07C 67/475; B01J 2231/49; B01J 2531/824; B01J 31/1815; B01J 2231/70
See application file for complete search history.

(56) References Cited

U.S. PATENT DOCUMENTS 4,599,476 A    7/1986  Drent

FOREIGN PATENT DOCUMENTS

| JP | S61-47422 A | 3/1986 |
|---|---|---|
| JP | S61-145126 A | 7/1986 |
| JP | H07-173107 A | 7/1995 |
| JP | 7-173107 | * 11/1995 |
| WO | 2011/099518 A1 | 8/2011 |

OTHER PUBLICATIONS

Atla et al. (Hydroesterification of 2-vinyl-6-methoxynaphthalene using palladium complexes containing chelating nitrogen ligands, Journal of Molecular Catalysis A: Chemical 307 (2009) 134-141).*
Giannoccaro et al. (Phenylacetylene carbonylation catalysed by Pd(II) and Rh(III) intercalated in zirconium phosphates, Appl. Organometal. Chem. 14, 581-589 (2000)).*
Okamoto et al. (Homogeneous Palladium Catalyst for the Oxidative Carbonylation of Bisphenol A to Polycarbonate in Propylene Carbonate, Journal of Applied Polymer Science, vol. 109, 758-762 (2008)).*
Jul. 8, 2014 International Search Report issued in International Patent Application No. PCT/JP2014/061056.

* cited by examiner

*Primary Examiner* — Yevegeny Valenrod
*Assistant Examiner* — Blaine G Doletski
(74) *Attorney, Agent, or Firm* — Oliff PLC

(57) ABSTRACT

A method for producing an ester compound including reacting a compound having at least one cyclic structure of a norbornene ring and a norbornadiene ring with an alcohol and carbon monoxide by using a palladium catalyst and an oxidizing agent, to thereby introduce ester groups to carbon atoms forming a double bond in the cyclic structure and obtain the ester compound, wherein the palladium catalyst comprises a palladium complex having a bipyridyl as a ligand.

7 Claims, 4 Drawing Sheets

METHOD FOR PRODUCING ESTER COMPOUND

TECHNICAL FIELD

The present invention relates to a method for producing an ester compound.

BACKGROUND ART

Conventionally, as a method for obtaining an ester compound, a method (a method utilizing so-called the oxidative alkoxycarbonylation reaction (esterification reaction)) has been known in which a norbornene-based compound having a carbon-carbon double bond is reacted with an alcohol and carbon monoxide by using a palladium catalyst to thereby introduce (add) ester groups to the carbon atoms forming the double bond and obtain an ester compound.

For example, International Publication No. WO 2011/099518 (PTL 1) discloses a method in which a norbornene is reacted with an alcohol and carbon monoxide by using a palladium catalyst and an oxidizing agent to thereby introduce ester groups to the carbon atoms forming the carbon-carbon double bond (olefinic double bond) in the norbornene and obtain an ester compound. PTL 1 discloses that palladium catalysts usable in the method include palladium chloride, palladium nitrate, palladium sulfate, palladium acetate, palladium propionate, palladium carbon, palladium alumina, palladium black, and the like.

Meanwhile, Japanese Unexamined Patent Application Publication No. Hei 7-173107 (PTL 2) discloses a method in which a norbornene such as norbornadiene, dicyclopentadiene, or bicyclo[2.2.1]hept-5-ene-2,3-dicarboxylic anhydride is reacted with an alcohol, carbon monoxide, and oxygen in the presence of a catalyst comprising (1) palladium metal or a compound thereof, (2) a copper compound, (3) a chlorine compound, and (4) a manganese or zinc compound to thereby introduce two carboxylic acid ester groups per carbon-carbon double bond contained in the bicyclo[2.2.1] ring of the norbornene. PTL 2 discloses that palladium metal and compounds thereof usable in this method include: materials in which palladium metal is supported on a support such as activated carbon, silica gel, alumina, silica-alumina, diatomite, magnesia, pumice, or molecular sieve; palladium metal such as palladium black; zero-valent palladium complexes such as palladium dibenzylideneacetone complex and tetrakis(triphenylphosphine)palladium; divalent palladium compounds including palladium halides such as palladium chloride and palladium bromide, inorganic acid salts of palladium such as palladium sulfate, palladium phosphate, and palladium nitrate, organic acid salts of palladium such as palladium acetate, palladium propionate, and palladium benzoate, palladium complexes such as bis(acetylacetonate) palladium, dichloro(cyclooctadiene)palladium, palladium chloride benzonitrile complex, and palladium chloride ammine complex; and the like.

CITATION LIST

Patent Literature

[PTL 1] International Publication No. WO 2011/099518
[PTL 2] Japanese Unexamined Patent Application Publication No. Hei 7-173107

SUMMARY OF INVENTION

Technical Problem

However, when a norbornene is reacted with an alcohol and carbon monoxide by using a conventional palladium catalyst as disclosed in PTL 1 or 2, the formation of by-products cannot necessarily be sufficiently suppressed, and the ester compound cannot necessarily be produced with a sufficient selectivity.

The present invention has been made in view of the above-described conventional technologies, and an object of the present invention is to provide a method for producing an ester compound by which the formation of the by-products can be sufficiently suppressed, and by which the ester compound can be efficiently produced with a sufficiently high selectivity.

Solution to Problem

The present inventors have conducted intensive study to achieve the object, and consequently found that, in a method for producing an ester compound, comprising reacting a compound having at least one cyclic structure of a norbornene ring and a norbornadiene ring with an alcohol and carbon monoxide by using a palladium catalyst and an oxidizing agent, to thereby introduce ester groups (alkoxycarbonyl groups) to the carbon atoms forming a double bond in the cyclic structure and obtain the ester compound, the use of a catalyst comprising a palladium complex having a bipyridyl as a ligand as the palladium catalyst makes it possible to sufficiently suppress the formation of by-products (especially, a polymerization product formed by the addition polymerization of the cyclic structure (the portion of the structure of the norbornene ring and/or the norbornadiene ring)), and to efficiently produce the ester compound with a sufficiently high selectivity. This finding has led to the completion of the present invention.

Specifically, a method for producing an ester compound of the present invention is a method for producing an ester compound comprising reacting a compound having at least one cyclic structure of a norbornene ring and a norbornadiene ring with an alcohol and carbon monoxide by using a palladium catalyst and an oxidizing agent, to thereby introduce ester groups to carbon atoms forming a double bond in the cyclic structure and obtain the ester compound, wherein the palladium catalyst comprises a palladium complex having a bipyridyl as a ligand.

In the method for producing an ester compound of the present invention, oxygen is preferably used as the oxidizing agent.

In addition, in the method for producing an ester compound of the present invention, when oxygen is used as the oxidizing agent, it is preferable to use a chlorine-containing compound, a copper compound other than a chloride, and a manganese compound other than a chloride in combination with the oxidizing agent, and more preferable to use manganese chloride, copper acetate, and manganese acetate in combination with the oxidizing agent.

Advantageous Effects of Invention

According to the present invention, it is possible to provide a method for producing an ester compound by which the formation of the by-products can be sufficiently suppressed, and by which the ester compound can be efficiently produced with a sufficiently high selectivity.

DESCRIPTION OF EMBODIMENTS

Figure 1:
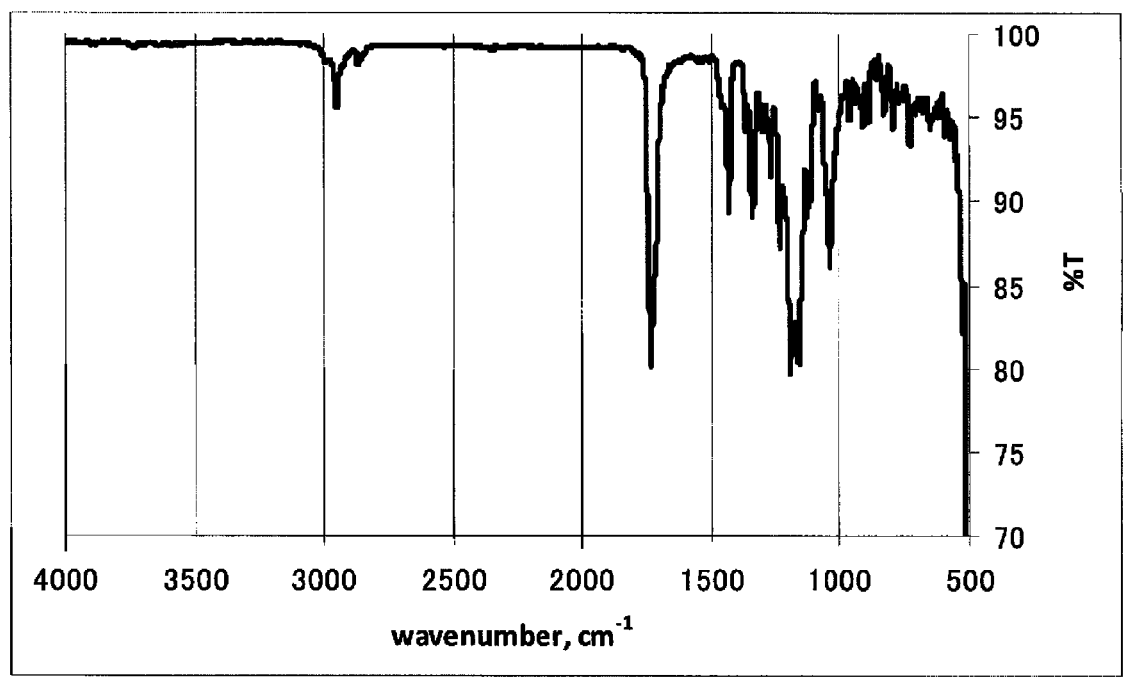
FIG. 1 is a graph showing an IR spectrum of a compound obtained in Example 1.

Hereinafter, the present invention will be described in detail based on preferred embodiments thereof.

A method for producing an ester compound of the present invention comprises: reacting a compound having at least one cyclic structure of a norbornene ring and a norbornadiene ring with an alcohol and carbon monoxide by using a palladium catalyst and an oxidizing agent, to thereby introduce ester groups to carbon atoms forming a double bond in the cyclic structure and obtain the ester compound, wherein the palladium catalyst comprises a palladium complex having a bipyridyl as a ligand.

The palladium catalyst according to the present invention comprises a palladium complex having a bipyridyl as a ligand. In the present invention, a palladium complex having a bipyridyl (2,2'-bipyridine or a derivative thereof) as a ligand is used as the catalyst as described above. The derivative of 2,2'-bipyridine may be one in which at least one of the hydrogen atoms in 2,2'-bipyridine is substituted with a different substituent (for example, an alkyl group, an aryl group, a hydroxyl group, a carboxyl group, an amino group, a nitro group, a sulfone group, a cyano group, or the like) and/or a different atom (for example, a halogen atom or the like), or the like. Examples of the derivatives of 2,2'-bipyridine include 4,4'-dimethyl-2,2'-bipyridine, 4,4'-diethyl-2,2'-bipyridine, 4,4'-di-normal-propyl-2,2'-bipyridine, 4,4'-diisopropyl-2,2'-bipyridine, 4,4'-di-normal-tertiary-butyl-2,2'-bipyridine, 4,4'-di-secondary-butyl-2,2'-bipyridine, 4,4'-di-tert-butyl-2,2'-bipyridine, 4,4'-diphenyl-2,2'-bipyridine, 3,3'-dihydroxy-2,2'-bipyridine, 4,4'-dihydroxy-2,2'-bipyridine, 4,4'-dicarboxy-2,2'-bipyridine, 4,4'-bis(methoxycarbonyl)-2,2'-bipyridine, 4,4'-bis(acetoxy)-2,2'-bipyridine, 4,4'-diamino-2,2'-bipyridine, 4,4'-dinitro-2,2'-bipyridine, 4,4'-disulfonyl-2,2'-bipyridine, 4,4'-dicyano-2,2'-bipyridine, 4,4'-dichloro-2,2'-bipyridine, 4,4'-dibromo-2,2'-bipyridine, and 4,4'-diiodo-2,2'-bipyridine. In addition, the bipyridyl (2,2'-bipyridine or a derivative thereof) used as a ligand of the palladium complex is particularly preferably 2,2'-bipyridine from the viewpoint of ease of synthesis of the palladium complex.

By using, as a catalyst, the palladium complex having a bipyridyl as a ligand, it is possible to sufficiently suppress the formation of by-products (especially, a polymerization product formed by addition polymerization of the cyclic structure), while efficiently producing the ester compound with a sufficiently high selectivity. Note that the polymerization product which may be formed as a by-product is difficult to separate from the ester compound. In addition, the present inventors have found that when an ester compound containing such a polymerization product is used as a raw material of a polyimide, or the like, side reactions due to the polymerization product may proceed and problems such as color development and embrittlement may occur in a polyimide film to be obtained. Accordingly, the more the amount of the polymerization product, which is one of the by-products, formed can be reduced in the formation of an ester compound, the better characteristics (for example, higher transparency and the like) the resultant polyimide can have, when the ester compound is used as a raw material of the polyimide, or the like. Meanwhile, in the cases where conventional palladium catalysts are used, even when the selectivity can be improved to some degree, the formation of the by-products (especially the polymerization product) cannot be necessarily sufficiently suppressed. When the obtained ester compound is directly used as a raw material of a polyimide, occurrence of the problems such as color development described above cannot be necessarily sufficiently suppressed. In this respect, the present invention, in which a palladium complex having a bipyridyl as a ligand is used as the palladium catalyst, makes it possible to suppress the formation of the by-products (especially, the polymerization product formed by addition polymerization of the cyclic structure) at an extremely advanced level, while producing the target product with a sufficiently advanced level of selectivity.

The palladium complex (the palladium complex having a bipyridyl as a ligand) is preferably a palladium complex represented by the following general formula (1):

Pd(bpy)X$_2$                 (1)

[in the formula, bpy represents a bipyridyl, and X represents a monovalent anionic ligand], because the effect of suppressing the formation of the by-products (especially, the polymerization product formed by addition polymerization of the cyclic structure) can be achieved at a further advanced level, while producing the target product with a sufficiently advanced level of selectivity.

X in the general formula (1) is a monovalent anionic ligand. The monovalent anionic ligand is not particularly limited, and only needs to be a monovalent ligand capable of coordinating to palladium. Among such monovalent anionic ligands, halogen ligands, an acetate ligand (OAc), an acetylacetone ligand (acac), alkyl ligands, a nitrile ligand, a hydride ligand, aryl ligands, and allyl ligands are preferable, and a chlorine ligand (Cl) and an acetate ligand (OAc) are more preferable from the viewpoint of the level of coordination ability to the palladium to which the bipyridyl is coordinated. In addition, the palladium complex represented by general formula (1) is preferably a palladium complex of the general formula (1) in which X is a chlorine atom (a palladium complex represented by formula: Pd(bpy)Cl$_2$), from the viewpoints that the formation of the polymerization product can be suppressed at a further advanced level, while enabling the selectivity to be improved to a further advanced level, and that the palladium complex is readily available. X in the formula (1) is particularly preferably chlorine (Cl) as described above.

In addition, a method for producing the palladium complex is not particularly limited, and a known method can be employed, as appropriate. For example, when the palladium complex of the general formula (1) in which X is chlorine (the palladium complex represented by Formula: Pd(bpy)Cl$_2$) is produced, it is possible to employ a method in which palladium chloride and 2,2'-bipyridyl are stirred in methanol, or the like. Note that the structure of the catalyst (for example, Pd(bpy)Cl$_2$ or the like) comprising the palladium complex having a bipyridyl as a ligand can be confirmed by NMR measurement or the like. In addition, a commercially available product ("Pd(bpy)Cl$_2$" manufactured by Sigma-Aldrich, or the like) may be used as the palladium complex having a bipyridyl as a ligand (more preferably the palladium complex represented by the general formula (1)).

Note that, in the present invention, the palladium complex having a bipyridyl as a ligand (more preferably the palladium complex represented by the general formula (1), and particularly preferably the palladium complex represented by the formula: Pd(bpy)Cl$_2$) is used as the palladium catalyst. However, another palladium catalyst may be mixed and used in the reaction system. In this case, 50% by atom or more (further preferably 70% by atom to 100% by atom) of all the palladium element present in the reaction system is preferably originated from the palladium (element) in the palladium complex having a bipyridyl as a ligand. If the ratio of the palladium element originated from the palladium in the palladium complex having a bipyridyl as a ligand is less than the lower limit, it tends to be impossible to sufficiently obtain the effect obtainable by using the palladium complex, it tends to be difficult to suppress the formation of the by-products, and it tends to be difficult to produce the ester compound with an advanced level of selectivity. Note that, as the other palladium catalyst, it is possible to use, as appropriate, any of known palladium-based catalyst components (palladium chloride, palladium nitrate, palladium sulfate, palladium acetate, palladium propionate, palladium carbon, palladium alumina, palladium black, and the like) which can be used for alkoxycarbonylation (esterification) of a carbon-carbon double bond (olefinic double bond) in a norbornene ring and a norbornadiene ring. In addition, it is preferable to use, as the palladium catalyst, the palladium complex having a bipyridyl as a ligand alone, from the viewpoints of suppressing the formation of the by-products at a further advanced level, and producing the ester compound with a further advanced level of selectivity.

Moreover, the oxidizing agent according to the present invention may be any, as long as the oxidizing agent is a compound or gas component capable of oxidizing Pd$^0$ to Pd$^{2+}$ when Pd$^{2+}$ in the palladium catalyst is reduced to Pd$^0$ during the reaction for introducing the ester groups (oxidative alkoxycarbonylation (esterification) reaction) (a compound or gas component capable of reoxidizing the reduced palladium catalyst). Known compounds and the like usable as reoxidizing agents for palladium catalysts can be used, as appropriate. Examples of the oxidizing agent include copper salts (preferably divalent copper salts: copper(II) chloride, copper(II) acetate, Cu(acac)$_2$, copper(II) benzoate, copper (II) carbonate, copper(II) nitrate, and the like); iron salts (iron chloride, iron acetate, iron sulfate, iron nitrate, and the like); manganese salts (preferably tetravalent manganese salts: manganese oxide and the like); chromium salts (potassium dichromate and the like); vanadium salts (vanadium acetate and the like); heteropoly acids (molybdovanadophosphoric acid and the like); hydrogen peroxide; gas components such as oxygen; and the like. As described above, a gas component such as oxygen or air may also be used as the oxidizing agent according to the present invention. This makes it possible to cause the reaction to efficiently proceed by using an atmospheric gas. In addition, more specific examples of the oxidizing agent include copper(II) chloride, copper(II) nitrate, copper(II) sulfate, copper(II) acetate, iron (III) chloride, iron(III) nitrate, iron(III) sulfate, iron(III) acetate, manganese dioxide, oxygen, and the like.

In addition, from the viewpoint of ease of the removal of by-products derived from the oxidizing agent, it is preferable to use a gas component such as oxygen (including oxygen in air) (particularly preferably oxygen) as the oxidizing agent for the oxidation of Pd$^0$ to Pd$^{2+}$. As described above, the use of a gas component such as oxygen as the oxidizing agent (especially the carrying out of the reaction in the presence of oxygen) makes it possible to cause the reaction to proceed with Pd$^0$ being oxidized to Pd$^{2+}$ more efficiently. Note that when oxygen is used as the oxidizing agent, oxygen gas (including oxygen in air) is used, with oxygen gas being replenished to the atmospheric gas. In such a case, the reaction can be carried out continuously, unless the palladium catalyst loses its activity. This enables the ester compound to be produced extremely efficiently.

In addition, in the reaction system using such an oxidizing agent, an auxiliary catalyst can be used with the oxidizing agent. As the auxiliary catalyst, known auxiliary catalysts usable in the reaction for introducing the ester groups (oxidative alkoxycarbonylation (esterification) reaction) can be used, as appropriate. In addition, as the auxiliary catalyst, a different kind of compound from the compound selected as the oxidizing agent may be selected and used, as appropriate (for example, when copper acetate is used as the oxidizing agent, a material other than copper acetate is used as the auxiliary catalyst, while when the oxidizing agent is other than copper acetate, copper acetate may be used as the auxiliary catalyst). Examples of the auxiliary catalyst include chlorine-containing compounds (including chlorides of metals such as copper, manganese, and zinc), copper compounds other than chlorides, manganese compounds other than chlorides, zinc compounds other than chlorides, and the like.

In addition, when oxygen is used as the oxidizing agent, it is preferable to use at least one selected from chlorine-containing compounds, copper compounds other than chlorides, and manganese compounds other than chlorides as the auxiliary catalyst, and more preferably to use a combination of a chlorine-containing compound, a copper compound other than a chloride, and a manganese compound other than a chloride as the auxiliary catalyst, from the viewpoint that the reaction can be caused to proceed more efficiently. Note that especially when a combination of a chlorine-containing compound, a copper compound other than a chloride, and a manganese compound other than a chloride is used in the case where oxygen is used as the oxidizing agent, it tends to be possible to cause the reaction to proceed further efficiently, and to carry out the reaction more continuously by using oxygen gas (including oxygen in air) with the oxygen gas being replenished to the atmospheric gas.

Meanwhile, examples of the chlorine-containing compounds include chlorine and chlorine solutions; hydrogen chloride and hydrogen chloride solutions; tertiary-alkyl chlorides such as tertiary-butyl chloride and tertiary-amyl chloride; organic chlorides which easily produce a chlorine ion such as acid chlorides including acetyl chloride, benzoyl chloride, and the like; chlorine-containing carbonic acid derivatives such as phosgene and methyl chloroformate; phosphorus chlorides such as phosphorus pentachloride; phosphorus oxychlorides such as phosphoryl trichloride; tellurium chlorides such as tellurium tetrachloride; thionyl chloride; chlorides and oxychlorides of metals of the group 4A such as titanium and zirconium, the group 5A such as vanadium and tantalum; the group 6A such as chromium and molybdenum; the group 7A such as manganese, the group 8 such as iron, cobalt, nickel, ruthenium, palladium, and platinum, the group 1B such as copper, the group 2B such as zinc and cadmium, the group 4B such as germanium and tin, and the group 5B such as antimony and bismuth with the valences of these chlorides and oxychlorides varying according to the metals; and the like. Note that when the chlorine ion concentration in the solution is increased by the chlorine-containing compound or the like, the redox potential of palladium tends to be lowered, and the reoxidation speed of palladium tend to be improved.

Of these chlorine-containing compounds, hydrogen chloride, phosphorus pentachloride, phosphoryl trichloride, vanadium oxytrichloride, chromium trichloride, manganese chloride, iron chloride, copper chloride, zinc chloride, tin chloride, and bismuth chloride are preferable from the viewpoint of the solubility in an organic solvent. From the viewpoint of the level of the activity in the reaction and from the viewpoint that a higher effect as an auxiliary catalyst can be obtained in the case where oxygen is used as the oxidizing agent, manganese chloride (particularly preferably manganese (II) chloride) is particularly preferable. In addition, one of these chlorine-containing compounds may be used alone, or two or more thereof may be used as a mixture.

Meanwhile, examples of the copper compounds other than chlorides (chlorine-containing compounds: copper chlorides) include inorganic acid salts of copper including copper halides other than chlorides, such as copper bromide, copper carbonate, copper nitrate, and the like, organic acid salts of copper such as copper acetate, copper propionate, copper stearate, and copper benzoate, copper complex compounds such as copper acetylatonate and copper benzoylacetonate, and the like. In addition, the valence of copper in such a compound is not particularly limited, and the copper may be monovalent or divalent.

The copper compound is preferably an inorganic or organic acid salt of copper from the viewpoint of the thermal stability of the compound. From the viewpoint of the solubility in an organic solvent, the copper compound is preferably copper nitrate, copper acetate, copper propionate, copper stearate, or copper benzoate. The copper compound is more preferably a copper acetate (particularly preferably copper(II) acetate), because a higher effect as an auxiliary catalyst can be obtained, when oxygen is used as the oxidizing agent. In addition, one of these copper compounds other than chlorides may be used alone, or two or more thereof may be used as a mixture.

In addition, examples of the manganese compounds other than chlorides (chlorine-containing compounds: manganese chlorides) include oxides, hydroxides, halides other than chlorides, carbonates, organic acid salts (acetic acid salts, propionic acid salts, stearic acid salts, divalent or tetravalent organic acid salts of succinic acid, phenylacetic acid, benzoic acid, phthalic acid, toluenesulfonic acid, and the like), complex compounds (acetylacetonate complexes, cyclopentadienyl complexes, carbonyl complexes, and the like) of manganese, and the like. In addition, the valence of manganese in such a compound is not particularly limited. The manganese is more preferably divalent, because a higher effect as the auxiliary catalyst can be obtained, when oxygen is used as the oxidizing agent. In other words, the manganese compound is preferably a manganese(II) salt.

Of these manganese compounds, inorganic or organic acid salts of copper are preferable from the viewpoint of the thermal stability of the compounds. Manganese acetate, manganese propionate, manganese stearate, manganese benzoate are preferable from the viewpoint of the solubility in an organic solvent. Manganese acetate (particularly preferably manganese(II) acetate) is more preferable from the viewpoint of suppressing the formation of the polymerization product. In addition, one of these manganese compounds may be used alone, or two or more thereof may be used as a mixture.

In addition, when a combination of a chlorine-containing compound, a copper compound other than a chloride, and a manganese compound other than a chloride is used as the auxiliary catalyst in a case where oxygen is used as the oxidizing agent, it is more preferable to use a combination of manganese chloride, copper acetate, and manganese acetate, because the formation of the by-products (especially the polymerization product) can be suppressed at a further advanced level, and the target product can be produced with a further advanced level of selectivity. As described above, when the oxidizing agent comprises oxygen, it is particularly preferable to use a combination of manganese chloride, copper acetate, and manganese acetate as the auxiliary catalyst in the present invention. Note that, when manganese chloride (particularly preferably $MnCl_2$), copper acetate (particularly preferably $Cu(OAc)_2$), and manganese acetate (particularly preferably $Mn(OAc)_2$) are used with oxygen (oxidizing agent), no metal compounds difficult to separate from the product are formed from these metal compounds, and the inclusion of metal compounds which are difficult to separate in the product is sufficiently suppressed. For this reason, a step of separating the product from the catalyst and the oxidizing agent tends to be simpler.

In addition, in the present invention, the compound having at least one cyclic structure of a norbornene ring and a norbornadiene ring is a raw material compound used for obtaining the ester compound by introducing ester groups to the carbon-carbon double bond (olefinic double bond) in the cyclic structure (hereinafter, the compound having at least one cyclic structure of a norbornene ring and a norbornadiene ring is simply referred to as "raw material compound" in some cases). The raw material compound will be described more specifically. The compound only needs to have, in its structure, at least one of a cyclic structure comprising a norbornene ring represented by the following structural formula (2):

[Chem. 1]

(2)

and a cyclic structure comprising a norbornadiene ring represented by the following structural formula (3):

[Chem. 2]

(3)

The other parts in the structure of the compound are not particularly limited. Specifically, the raw material compound only needs to have the cyclic structure, and examples thereof include optionally substituted norbornenes; optionally substituted norbornadienes; compounds in each of which an optionally substituted norbornene and/or norbornadiene is bound to another organic compound (for example, a linear hydrocarbon, a branched hydrocarbon, or an unsaturated hydrocarbon); condensed-ring compounds or spiro compounds each formed from at least one of a norbornene ring and a norbornadiene ring and another cyclic hydrocarbon (which may have a substituent and may have a heteroatom in the ring); and the like.

As described above, the raw material compound only needs to have the cyclic structure, and the so-called norbornenes, norbornadienes, derivatives thereof, and the like can be used as appropriate. In addition, although the raw material compound is not particularly limited, at least one of compounds represented by the following general formulae (4) to (11) can be preferably used:

[Chem. 3]

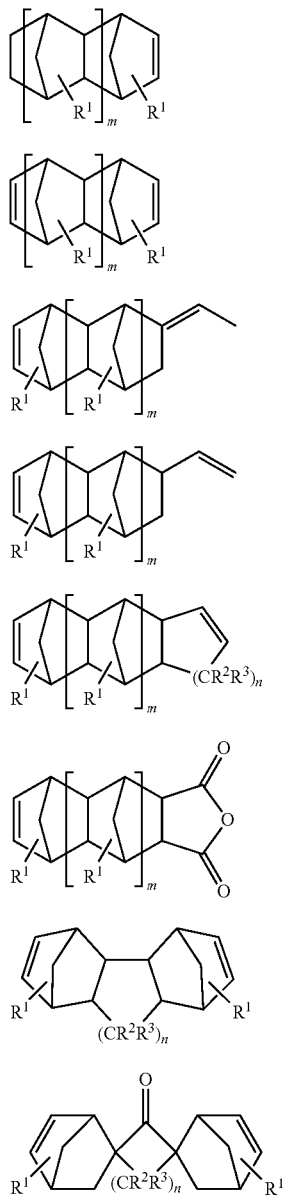

[in the formulae, $R^1$s, $R^2$s, and $R^3$s each independently represent one selected from the group consisting of a hydrogen atom, alkyl groups having 1 to 10 carbon atoms, and a fluorine atom, n represents an integer of 0 to 12, and m represents an integer of 0 to 5.

If the number of carbon atoms of the alkyl group which can be selected as each $R^1$ in the general formulae (4) to (11) exceeds the upper limit, the production and purification tend to be difficult. In addition, from the viewpoint of the ease of production and purification, the number of carbon atoms of the alkyl group which can be selected as $R^1$ is preferably 1 to 5, and more preferably 1 to 3. In addition, the alkyl group which can be selected as $R^1$ may be linear or branched. Moreover, $R^1$s in the above-described general formulae (4) to (11) are more preferably each independently a hydrogen atom or an alkyl group having 1 to 10 carbon atoms from the viewpoint of the ease of production and purification. Especially, from the viewpoints that the raw material is readily available and that the purification is easier, $R^1$s are more preferably each independently a hydrogen atom, a methyl group, an ethyl group, a n-propyl group, or an isopropyl group, and particularly preferably a hydrogen atom or a methyl group. In addition, the multiple $R^1$s in each of the formulae are particularly preferably the same, from the viewpoints of the ease of production and purification and the like.

In addition, the alkyl groups having 1 to 10 carbon atoms which can be selected as $R^2$s and $R^3$s in the general formulae (4) to (11) are the same as the alkyl groups having 1 to 10 carbon atoms which can be selected as $R^1$s. Of these substituents, the substituent which can be selected as each of $R^2$s and $R^3$s is preferably a hydrogen atom or an alkyl group having 1 to 10 carbon atoms (more preferably 1 to 5, and further preferably 1 to 3 carbon atoms), and particularly preferably a hydrogen atom or a methyl group, from the viewpoint of ease of purification.

In addition, n in each of the above-described general formulae (4) to (11) represents an integer of 0 to 12. If the value of n exceeds the upper limit, it is difficult to produce and purify the compound represented by each of the above-described general formulae (4) to (11). In addition, an upper limit value of the numeric value range of n in the general formulae (4) to (11) is more preferably 5, and particularly preferably 3, from the viewpoint that the production and purification are easier. Meanwhile, a lower limit value of the numeric value range of n in the general formulae (4) to (11) is more preferably 1, and particularly preferably 2, from the viewpoint of the stability of the raw material. In sum, n in the general formulae (4) to (11) is particularly preferably an integer of 2 to 3.

Moreover, m in each of the above-described general formulae (4) to (11) represents an integer of 0 to 5. If the value of m exceeds the upper limit, it is difficult to produce and purify the compound represented by each of the above-described general formulae (4) to (11). In addition, an upper limit value of the numeric value range of m in the general formulae (4) to (11) is more preferably 3, and particularly preferably 1, from the viewpoints of production and purification. Meanwhile, a lower limit value of the numeric value range of m in the general formulae (4) to (11) is particularly preferably 0, from the viewpoints of production and purification. In sum, m in the general formulae (4) to (11) is particularly preferably an integer of 0 to 1.

Moreover, more specific examples of the raw material compounds represented by the general formulae (4) to (11) include compounds represented by the following general formulae (12) to (25) and the like:

[Chem. 4]

(12) 

(13) 

(14) 

(15) 

(16) 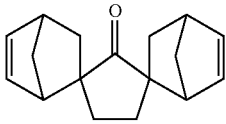

(17) 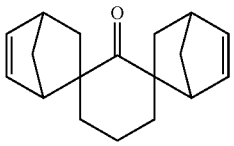

(18) 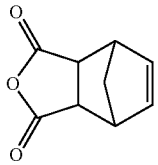

(19) 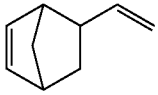

(20) 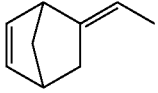

(21) 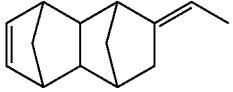

(22) 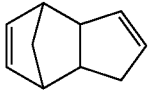

(23) 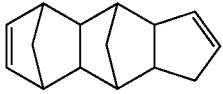

-continued

(24) 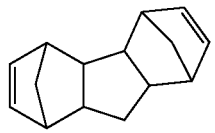

(25) 

In addition, a method for preparing the raw material compound is not particularly limited, and a known method can be employed, as appropriate. For example, when a compound (spiro compound) represented by the above-described general formula (11) is used as the raw material compound, the method for preparing a spiro compound disclosed in International Publication No. WO2011/099518 may be used, as appropriate.

In addition, the alcohol according to the present invention is not particularly limited, as long as the alcohol can be used for the esterification reaction of a norbornene. Especially, from the viewpoint of the ease of production and purification, the alcohol is preferably an alcohol represented by the following general formula (26):

$$R^4OH \qquad (26)$$

[in the formula (26), $R^4$ represents one selected from the group consisting of alkyl groups having 1 to 10 carbon atoms, cycloalkyl groups having 3 to 10 carbon atoms, alkenyl groups having 2 to 10 carbon atoms, aryl groups having 6 to 20 carbon atoms, and aralkyl groups having 7 to 20 carbon atoms]. In other words, it is preferable to use, as the alcohol, an alkyl alcohol having 1 to 10 carbon atoms, a cycloalkyl alcohol having 3 to 10 carbon atoms, an alkenyl alcohol having 2 to 10 carbon atoms, an aryl alcohol having 6 to 20 carbon atoms, or an aralkyl alcohol having 7 to 20 carbon atoms.

The alkyl group which can be selected as $R^4$ in the general formula (26) is an alkyl group having 1 to 10 carbon atoms. If the number of carbon atoms of the alkyl group exceeds 10, it tends to be difficult to purify the obtained ester compound. In addition, the number of carbon atoms of the alkyl group which can be selected as $R^4$ is more preferably 1 to 5, and further preferably 1 to 3, from the viewpoint that the production and the purification are easier. In addition, the alkyl group which can be selected as $R^4$ may be linear or branched.

Meanwhile, the cycloalkyl group which can be selected as $R^4$ in the general formula (26) is a cycloalkyl group having 3 to 10 carbon atoms. If the number of carbon atoms of the cycloalkyl group exceeds 10, it tends to be difficult to produce and purify the obtained ester compound. The number of carbon atoms of the cycloalkyl group which can be selected as $R^4$ is more preferably 3 to 8, and further preferably 5 to 6, from the viewpoint that the production and the purification are easier.

Moreover, the alkenyl group which can be selected as $R^4$ in the above-described general formula (26) is an alkenyl group having 2 to 10 carbon atoms. If the number of carbon atoms of the alkenyl group exceeds 10, it tends to be difficult to produce and purify the obtained ester compound. In addition, the number of carbon atoms of the alkenyl group which can be selected as $R^4$ is more preferably 2 to 5, and further preferably 2 to 3, from the viewpoint that the production and the purification are easier.

Meanwhile, the aryl group which can be selected as $R^4$ in the above-described general formula (26) is an aryl group having 6 to 20 carbon atoms. If the number of carbon atoms of the aryl group exceeds 20, it tends to be difficult to produce and purify the obtained ester compound. In addition, the number of carbon atoms of the aryl group which can be selected as $R^4$ is more preferably 6 to 10, and further preferably 6 to 8, from the viewpoint that the production and the purification are easier.

Meanwhile, the aralkyl group which can be selected as $R^4$ in the above-described general formula (26) is an aralkyl group having 7 to 20 carbon atoms. If the number of carbon atoms of the aralkyl group exceeds 20, it tends to be difficult to produce and purify the obtained ester compound. In addition, the number of carbon atoms of the aralkyl group which can be selected as $R^4$ is more preferably 7 to 10, and further preferably 7 to 9, from the viewpoint that the production and the purification are easier.

Moreover, from the viewpoint that the obtained ester compound is easier to produce and purify, $R^4$ in the above-described general formula (26) is preferably each independently a hydrogen atom, a methyl group, an ethyl group, a n-propyl group, an isopropyl group, a n-butyl group, an isobutyl group, a sec-butyl group, a t-butyl group, a 2-ethylhexyl group, a cyclohexyl group, an allyl group, a phenyl group, or a benzyl group, and is particularly preferably a methyl group.

Examples of the alcohol include methanol, ethanol, butanol, allyl alcohol, cyclohexanol, benzyl alcohol, and the like. Of these alcohols, methanol and ethanol are more preferable, and methanol is particularly preferable, from the viewpoint that the obtained ester compound is easier to produce and purify. In addition, one of these alcohols may be used alone, or two or more thereof may be used as a mixture.

Meanwhile, the reaction in which the compound (raw material compound) having at least one cyclic structure of a norbornene ring and a norbornadiene ring is reacted with an alcohol and carbon monoxide to introducing ester groups to carbon atoms forming a double bond in the cyclic structure is a reaction (oxidative alkoxycarbonylation reaction: hereinafter, simply referred to as "esterification reaction" in some cases) in which the ester compound is obtained by reacting the raw material compound with the alcohol ($R^4OH$) and carbon monoxide (CO) by using the palladium catalyst having a bipyridyl as a ligand and the oxidizing agent, to introduce an ester group represented by the following general formula (27):

—COOR$^4$  (27)

[in formula (27), $R^4$ has the same meaning as that of $R^4$ in the above-described general formula (26)] to each of the two carbon atoms forming a double bond (olefinic double bond (—C=C—)) of the cyclic structure (norbornene ring and/or norbornadiene ring) contained in the raw material compound (in each position in which the ester group is introduced, each of $R^4$s may be the same or different). Note that, for describing such an esterification reaction, the reactions occurring at the portion of the cyclic structure are described by taking the following reaction formulae (I) and (II) as examples (note that the reaction formula (I) shows, as an example of the reactions occurring at the portion of the cyclic structure, a reaction in which ester groups are introduced to a double bond contained in the cyclic structure comprising a norbornene ring in the raw material compound (the structure represented by the above-described structural formula (2)), whereas the reaction formula (II) shows, as an example of the reactions occurring in the portion of the cyclic structure, a reaction in which ester groups are introduced to double bonds contained in the cyclic structure comprising a norbornadiene ring in the raw material compound (the structure represented by the above-described structural formula (3))). The reactions occurring at the portion of the cyclic structure (the reaction in which ester groups are introduced to the portion of the cyclic structure) are reactions represented by the following reaction formulae (I) and (II)

[Chem. 5]

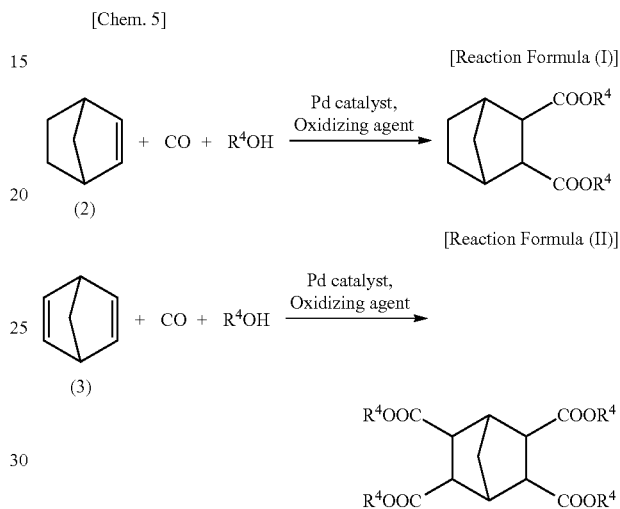

[in the reaction formulae (I) and (II), $R^4$s have the same meaning as that of $R^4$ in the above-described general formula (27); note that the multiple $R^4$s may be the same or different]. In the present invention, as in the reactions shown in the reaction formulae (I) and (II), the esterification reaction is conducted by reacting the raw material compound having at least one cyclic structure of a norbornene ring and a norbornadiene ring with the alcohol and carbon monoxide, so that an ester group is introduced (added) to each of the carbon atoms forming each carbon-carbon double bond in the cyclic structure (norbornene ring and/or norbornadiene ring) in the raw material compound, and the ester compound (the compound in which at least the portion of the cyclic structure in the raw material compound is esterified as shown in the reaction formula (I) and/or (II)) is obtained. Moreover, such an esterification reaction is described, while a case where, for example, a spiro compound represented by the above-described general formula (11) is used as the raw material compound is taken as an example. The esterification reaction is a reaction as represented by the following reaction formula (III):

[Chem. 6]

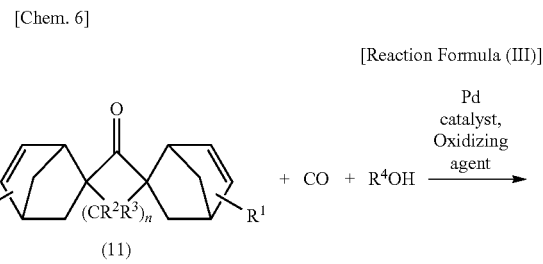

-continued

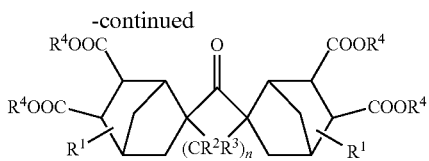

[in the reaction formula (III), $R^1$s, $R^2$s, $R^3$s, and n have the same meanings as those of $R^1$s, $R^2$s, $R^3$s, and n in the above-described general formula (11), and $R^4$s have the same meanings as those of $R^4$s in the above-described general formula (26); note that the multiple $R^4$s may be the same or different]. Note that, in the esterification reaction, when the raw material compound is a compound having a structure containing a double bond (for example, a chainlike or cyclic unsaturated hydrocarbon) other than the cyclic structure (norbornene ring and norbornadiene ring), ester groups may be introduced also to the carbon atoms forming the double bond in the structure other than the cyclic structure, along with the above-described esterification reaction. Meanwhile, when the raw material compound itself has a carboxylic anhydride group (—CO—O—CO—), the carboxylic anhydride group may be reacted with the alcohol to form ester groups, along with the above-described esterification reaction.

The amount of the palladium catalyst used in the esterification reaction is preferably such that the mole amount of palladium (metal) in the palladium catalyst (the mole amount of the palladium catalyst in terms of Pd metal) is a mole amount of $1.0 \times 10^{-6} \times n$ times to $0.10 \times n$ times (more preferably $1.0 \times 10^{-6} \times n$ times to $0.05 \times n$ times, further preferably $5.0 \times 10^{-6} \times n$ times to $1.0 \times 10^{-2} \times n$ times, and particularly preferably $2.5 \times 10^{-5} \times n$ times to $2.5 \times 10^{-3} \times n$ times) per mole of the raw material compound, where n represents the total number of carbon-carbon double bonds in the cyclic structure (norbornene ring or norbornadiene ring) in the raw material compound (n is an integer of 1 or greater) (For example, when the total number n is 1, the mole amount of palladium in the palladium catalyst is preferably $1.0 \times 10^{-6}$ to 0.10 moles per mole of the raw material compound.). If the amount (mole amount) of the palladium catalyst used is less than the lower limit, the reaction rate tends to decrease, and the percentage yield of the target product tends to decrease. Meanwhile, if amount of the palladium catalyst used exceeds the upper limit, the reaction rate tends to be greatly improved, and the reaction tends to be difficult to control, actually.

In addition, the amount (total amount) of the oxidizing agents used in the esterification reaction is preferably a mole amount which is $2.0 \times (1/m) \times n$ times to $4.0 \times (1/m) \times n$ times (more preferably $2.0 \times (1/m) \times n$ times to $3.0 \times (1/m) \times n$ times, and particularly preferably $2.0 \times (1/m) \times n$ times to $2.5 \times 1/m \times n$ times) per mole of the raw material compound, where m represents the number of electrons received by one mole of the oxidizing agents in the reduction reaction (for example, when the oxidizing agent is oxygen, m is 4), and n represents the total number of carbon-carbon double bonds in the cyclic structure (norbornene ring or norbornadiene ring) in the raw material compound. (For example, when the number m of electrons is 1, and the total number n is 1, the amount of the oxidizing agents used is preferably 2.0 to 4.0 moles per mole of the raw material compound.). If the amount (mole amount) of the oxidizing agents used is less than the lower limit, it tends to be impossible to efficiently reoxidize palladium, and the percentage yield of the target product tends to decrease. Meanwhile, if the amount of the oxidizing agents used exceeds the upper limit, the reaction rate tends to be improved greatly, and the reaction tends to be difficult to control, actually.

In addition, when a chlorine-containing compound, a copper compound other than a chloride, and a manganese compound other than a chloride are used in combination with the oxidizing agent, the content of the chlorine-containing compound (particularly preferably manganese chloride) is preferably such an amount that the mole amount of chlorine atoms in the chlorine-containing compound can be $2.5 \times 10^{-2} \times n$ times to $0.20 \times n$ times (more preferably $3.0 \times 10^{-2} \times n$ times to $0.50 \times n$ times, and particularly preferably $3.5 \times 10^{-2} \times n$ times to $0.10 \times n$ times) per mole of the raw material compound, where n represents the total number of carbon-carbon double bonds in the cyclic structure (norbornene ring or norbornadiene ring) in the raw material compound (For example, when the total number n is 1, the mole amount of chlorine atoms in the chlorine-containing compound (particularly preferably manganese chloride) is preferably $2.5 \times 10^{-2}$ to 0.20 moles per mole of the raw material compound.). If the content of the chlorine-containing compound is less than the lower limit, it tends to be difficult to efficiently reoxidize palladium, and the percentage yield of the target product tends to decrease. Meanwhile, if the content of the chlorine-containing compound exceeds the upper limit, the effect of suppressing the by-production of the polymerization product tends to decrease.

Note that, from the same viewpoint, when the chlorine-containing compound is manganese chloride ($MnCl_2$), the amount of manganese chloride used is preferably a mole amount of $1.2 \times 10^{-2} \times n$ times to $0.10 \times n$ times (more preferably $1.4 \times 10^{-2} \times n$ times to $7.0 \times 10^{-2} \times n$ times, and particularly preferably $1.6 \times 10^{-2} \times n$ times to $3.5 \times 10^{-2} \times n$ times) per mole of the raw material compound, where n represents the total number of carbon-carbon double bonds in the cyclic structure (norbornene ring or norbornadiene ring) in the raw material compound. If the content ratio of manganese chloride is less than the lower limit, it tends to be difficult to efficiently reoxidize palladium, and the percentage yield of the target product tends to decrease. Meanwhile, if the content ratio of manganese chloride exceeds the upper limit, the effect of suppressing the by-production of the polymerization product tends to decrease.

In addition, when a chlorine-containing compound, a copper compound other than a chloride, and a manganese compound other than a chloride are used in combination with the oxidizing agent, the amount of the copper compound (particularly preferably copper acetate) used is preferably such an amount that the mole amount of copper in the copper compound can be $2.0 \times 10^{-2} \times n$ times to $0.1 \times n$ times (more preferably $2.5 \times 10^{-2} \times n$ times to $7.5 \times 10^{-2} \times n$ times, and particularly preferably $2.5 \times 10^{-2} \times n$ times to $5.0 \times 10^{-2} \times n$ times) per mole of the raw material compound, where n represents the total number of carbon-carbon double bonds in the cyclic structure (norbornene ring or norbornadiene ring) in the raw material compound (For example, when the total number n is 1, the mole amount of copper in the copper compound (particularly preferably copper acetate) is preferably $2.0 \times 10^{-2}$ to 0.1 moles per mole of the raw material compound.). If the content of the copper compound is less than the lower limit, it tends to be difficult to efficiently reoxidize palladium, and the percentage yield of the target product tends to decrease. Meanwhile, if the content of the copper compound exceeds the upper limit, a purification step for removing copper tends to be complicated.

Moreover, when a chlorine-containing compound, a copper compound other than a chloride, and a manganese compound other than a chloride are used in combination with the oxidizing agent, the content of the manganese compound (particularly preferably manganese acetate) is preferably such an amount that the mole amount of manganese in the manganese compound can be $2.0 \times 10^{-2} \times n$ times to $0.2 \times n$ times (more preferably $4.0 \times 10^{-2} \times n$ times to $0.15 \times n$ times, and particularly preferably $7.0 \times 10^{-2} \times n$ times to $0.1 \times n$ times) per mole of the raw material compound, where n represents the total number of carbon-carbon double bonds in the cyclic structure (norbornene ring or norbornadiene ring) in the raw material compound (For example, when the total number n is 1, the mole amount of manganese in the manganese compound (particularly preferably manganese acetate) is preferably $2.0 \times 10^{-2}$ to $0.2$ moles per mole of the raw material compound.). If the content of the manganese compound is less than the lower limit, the effect of suppressing the by-production of the polymerization product tends to decrease. Meanwhile, if the content of the manganese exceeds the upper limit, a purification step for removing manganese tends to be complicated.

In addition, when a chlorine-containing compound, a copper compound other than a chloride, and a manganese compound other than a chloride are used in combination with the oxidizing agent, the atomic ratio ([palladium]:[chlorine]) of palladium in the palladium catalyst to chlorine atoms in the chlorine-containing compound is preferably $1:2.5 \times 10^2$ to $1:2.0 \times 10^3$ (more preferably $1:3.0 \times 10^2$ to $1:1.0 \times 10^3$, and further preferably $1:5.0 \times 10^2$ to $1:1.0 \times 10^3$). If the content of chlorine atoms is less than the lower limit, it tends to be difficult to efficiently reoxidize palladium, and the percentage yield of the target product tends to decrease. Meanwhile, if the content of chlorine atoms exceeds the upper limit, the effect of suppressing the by-production of the polymerization product tends to decrease.

In addition, when a chlorine-containing compound, a copper compound other than a chloride, and a manganese compound other than a chloride are used in combination with the oxidizing agent, the atomic ratio ([palladium]:[copper]) of palladium in the palladium catalyst to copper in the copper compound in terms of metal is preferably $1:2.0 \times 10^2$ to $1:1.0 \times 10^3$ (more preferably $1:2.5 \times 10^2$ to $1:7.5 \times 10^2$, and further preferably $1:2.5 \times 10^2$ to $1:5.0 \times 10^2$). If the content ratio of the copper compound is less than the lower limit, it tends to be difficult to efficiently reoxidize palladium, and the percentage yield of the target product tends to decrease. Meanwhile, if the content ratio of the copper compound exceeds the upper limit, a purification step for removing copper tends to be complicated.

Moreover, when a chlorine-containing compound, a copper compound other than a chloride, and a manganese compound other than a chloride are used in combination with the oxidizing agent, the atomic ratio ([palladium]:[manganese]) of palladium in the palladium catalyst to manganese in the manganese compound is preferably $1:4.0 \times 10^2$ to $1:4.0 \times 10^3$ (more preferably $1:7.0 \times 10^2$ to $1:3.0 \times 10^3$, and further preferably $1:1.0 \times 10^3$ to $1:2.5 \times 10^3$). If the content ratio of the copper compound is less than the lower limit, the effect of suppressing the by-production of the polymerization product tends to decrease. Meanwhile, if the content ratio of the copper compound exceeds the upper limit, a purification step for removing manganese tends to be complicated.

Meanwhile, the amount of the alcohol used in the esterification reaction is not particularly limited, as long as the ester compound can be obtained with the amount. The amount of the alcohol used can be set, as appropriate, according to the kind of the raw material compound and the like. For example, it is possible to add the alcohol in an amount equal to or more than an amount (theoretical amount) theoretically necessary for obtaining the ester compound by the esterification of the raw material compound, and use the excessive portion of the alcohol itself as the solvent.

In addition, the amount of carbon monoxide used in the esterification reaction is not particularly limited, as long as the ester compound can be obtained with the amount. The amount of carbon monoxide used can be set, as appropriate, according to the kind of the raw material compound and the like. For example, it is possible to use carbon monoxide in an amount equal to or more than an amount (theoretical amount) theoretically necessary for obtaining the ester compound by the esterification of the raw material compound.

As described above, it is only necessary that the carbon monoxide (CO) in an amount necessary for the esterification be supplied, as appropriate, to the reaction system, in the present invention. For this reason, the gas for supplying the carbon monoxide to the reaction system may be high-purity carbon monoxide gas or a gas other than high-purity carbon monoxide gas. For example, it is possible to use carbon monoxide, a mixture gas obtained by mixing carbon monoxide with a gas inactive in the esterification reaction (for example, nitrogen or the like), or the like, and further it is also possible to use synthetic gas, coal gas, or the like. In addition, the gas for supplying carbon monoxide to the reaction system is preferably carbon monoxide or a mixture gas of carbon monoxide with another gas (nitrogen, air, oxygen, hydrogen, carbon dioxide, argon, or the like), from the viewpoint that no influence is exerted on any of the catalyst, the oxidizing agent, and the auxiliary catalysts such as copper acetate, manganese chloride, and manganese acetate. It is more preferable to use a mixture gas containing carbon monoxide, a gas inactive in the esterification reaction (for example, nitrogen or the like), and oxygen (including oxygen in air) from the viewpoint that oxygen (including oxygen in air) is used to cause the reaction to proceed more efficiently. In addition, the carbon monoxide (CO) may be supplied to the reaction system by introducing carbon monoxide (CO) into the atmospheric gas, and the atmospheric gas may consequently form the above-described mixture gas.

In addition, it is preferable to use a solvent for the reaction (esterification reaction) of the raw material compound with the alcohol and carbon monoxide. The solvent is not particularly limited, and various solvents can be used as appropriate. It is preferable that the alcohol (for example, methanol, ethanol, propanol, or the like) used for the esterification reaction itself be used as the solvent, while being used as a raw material for the reaction. In addition, it is also possible to add another solvent to the alcohol and use in the esterification reaction. Examples of the other solvent include aromatic solvents such as benzene, toluene, xylene, and chlorobenzene; ether-based solvents such as ether, THF, and dioxane; ester-based solvents such as ethyl acetate; hydrocarbon-based solvents such as hexane, cyclohexane, heptane, and pentane; nitrile-based solvents such as acetonitrile and benzonitrile; halogen-containing solvents such as methylene chloride and chloroform; ketone-based solvents such as acetone and MEK; and amide-based solvents such as DMF, NMP, DMI, and DMAc.

In addition, the concentration of the raw material compound in the solvent is preferably 0.05 to 0.30 mol/L, and more preferably 0.10 to 0.20 mol/L. If the concentration is less than the lower limit, the reaction rate tends to decrease, and the percentage yield of the target product tends to decrease. Meanwhile, if the concentration exceeds the upper limit, the reaction rate tends to be improved greatly, and the reaction tends to be difficult to control, actually. In addition, from the same viewpoint, the concentration of the raw material compound in the solvent is preferably 12 to 72 g/L, and more preferably 24 to 48 g/L.

Moreover, when an acid is by-produced from the oxidizing agent or the like in the esterification reaction, a base may be further added to remove the acid. The base is preferably a fatty acid salt such as sodium acetate, sodium propionate, or sodium butyrate. In addition, the amount of the base used may be adjusted, as appropriate, according to the amount of the acid generated and the like.

In addition, a reaction temperature condition for the esterification reaction is not particularly limited, and is preferably 60 to 150° C. (more preferably 80 to 120° C., and further preferably 80 to 100° C.). If the reaction temperature exceeds the upper limit, the raw material compound tends to partially decompose, and the percentage yield tends to decrease. Meanwhile, if the reaction temperature is lower than the lower limit, the reaction rate tends to decrease. In addition, the reaction time of the esterification reaction is not particularly limited, and is preferably about 30 minutes to 24 hours.

In addition, the atmospheric gas in the esterification reaction is not particularly limited, and a gas usable for an esterification reaction can be used, as appropriate. For example, the atmospheric gas may be carbon monoxide or a mixture gas of carbon monoxide with another gas (nitrogen, air, oxygen, hydrogen, carbon dioxide, argon, or the like). From the viewpoint that no influence is exerted on the catalyst or the oxidizing agent, the atmospheric gas is preferably a mixture gas of carbon monoxide with a gas inactive in the esterification reaction (nitrogen, argon, or the like). From the viewpoint that oxygen (including oxygen in air) in the atmospheric gas is used as the oxidizing agent to cause the reaction to proceed more efficiently, it is preferable to use a mixture gas containing carbon monoxide, a gas inactive in the esterification reaction (for example, nitrogen or the like), and oxygen (including oxygen in air).

In addition, a pressure condition (a pressure condition of the atmospheric gas: when the reaction is carried out in a reaction vessel, a pressure condition of the gas in the vessel) in the esterification reaction is preferably 1.0 MPa to 10 MPa, preferably 2.0 MPa to 8.0 MPa, and further preferably 3.0 MPa to 6.0 MPa. If the pressure condition is lower than the lower limit, the reaction rate tends to decrease, and the percentage yield of the target product tends to decrease. Meanwhile, if the pressure condition exceeds the upper limit, the reaction rate tends to be improved greatly, and the reaction tends to be difficult to control, actually. Note that a reaction vessel used for the esterification reaction is not particularly limited, and a known reaction vessel can be used, as appropriate. For example, an autoclave or the like may be used to carry out the reaction under the above-described pressure condition.

In addition, when a mixture gas containing carbon monoxide, a gas inactive in the esterification reaction (for example, nitrogen or the like), and oxygen (including oxygen in air) is used as the atmospheric gas, the volume ratio ([carbon monoxide]:[inactive gas]:[oxygen]) of carbon monoxide, the gas inactive in the esterification reaction, and oxygen is preferably 0.30:3.60:0.10 to 1.50:2.25:0.25, and more preferably 0.50:3.30:0.20 to 1.0:2.75:0.25. If the volume ratio of carbon monoxide is lower than the lower limit, the amount of the polymerization product formed tends to increase. Meanwhile, if the volume ratio of carbon monoxide exceeds the upper limit, the activity of the target reaction tends to decrease, because the concentration of carbon monoxide dissolved in the alcohol increases excessively. In addition, if the volume ratio of oxygen is less than the lower limit, it tends to be impossible to efficiently reoxidize palladium. Meanwhile, if the volume ratio of oxygen exceeds the upper limit, a reaction tends to proceed between oxygen and carbon monoxide, and the reaction tends to be difficult to control.

In addition, after the esterification reaction is carried out as described above, a purification step such as recrystallization may be conducted, as appropriate, to obtain the ester compound with a higher purity. A method for the purification is not particularly limited, and a known method can be employed, as appropriate. Note that the thus obtained ester compound is a compound in which ester groups (alkoxycarbonyl groups) are introduced to at least the carbon atoms forming a double bond in the cyclic structure.

As described above, in the present invention, ester groups are introduced to the carbon atoms forming a double bond in the cyclic structure (the structure of a norbornene ring and/or a norbornadiene ring) by using the palladium catalyst (an olefinic double bond in the cyclic structure is subjected to bisalkoxycarbonylation). Thus, the ester compound can be produced with a sufficiently high selectivity, while the formation of the by-products (especially, the polymerization product formed by the addition polymerization of the portion of the cyclic structure) is sufficiently suppressed. In other words, according to the present invention, the ester compound can be produced with a sufficiently high selectivity, and the formation of the by-products, which are difficult to separate because of emulsification upon extraction and which are difficult to sufficiently separate and remove even by purification such as recrystallization, can be sufficiently suppressed. Hence, the decrease in percentage yield can be sufficiently suppressed. In addition, the method for producing an ester compound of the present invention makes it possible to cause the reaction to proceed highly selectively, and hence the ester compound can be produced industrially advantageously.

EXAMPLES

Hereinafter, the present invention is described more specifically on the basis of Examples and Comparative Examples; however, the present invention is not limited to Examples below.

Example 1

To a 120 ml HASTELLOY (registered trademark) autoclave (manufactured by NITTOU HANNNOUKI KABU-SHIKI-GAISHA), copper acetate monohydrate (25.7 mg, 0.129 mmol), manganese acetate tetrahydrate (121.2 mg, 0.496 mmol), 17 mL of methanol, and a norbornene compound (619.1 mg, 2.58 mmol, raw material compound) represented by the following general formula (16) were added:

[Chem. 7]

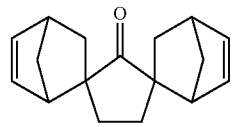

(16)

Then, 1.94 mL of a methanol solution of manganese chloride tetrahydrate (concentration: 10.0 g/L) prepared under a nitrogen atmosphere was added to the autoclave. In this manner, a mixture was obtained. In addition, a Pd(bpy) Cl$_2$ solution in which Pd(bpy)Cl$_2$ (3.4 mg, 2.58×10$^{-4}$ mmol) manufactured by Sigma-Aldrich was dissolved in 40 mL of methanol was prepared separately. Subsequently, a mixture liquid for reaction was obtained by adding 1.0 mL of the Pd(bpy)Cl$_2$ solution to the mixture in the autoclave.

Next, the autoclave was hermetically sealed, and nitrogen was introduced to achieve a pressure in the vessel (autoclave) of 6.0 MPaG, and this state was kept for 5 minutes (gas-tightness test). Subsequently, nitrogen was released from the autoclave back to atmospheric pressure (0 MPaG), and carbon monoxide was introduced to achieve a pressure in the vessel of 1.0 MPaG. Subsequently, nitrogen was introduced to achieve a pressure in the autoclave of 2.8 MPaG. Next, air was introduced to achieve a pressure in the vessel of 4.0 MPaG. In this manner, a mixture gas having a partial pressure ratio of carbon monoxide, nitrogen, and air of 1.0:1.8:1.2 with a total pressure of 4 MPaG was introduced into the autoclave, and an atmosphere of the mixture gas was created in the autoclave.

Subsequently, the mixture liquid in the autoclave was heated to 100° C. with stirring at a number of revolutions of 500 rpm, and allowed to react for 4 hours. After that, the mixture liquid in the autoclave was allowed to cool naturally to about room temperature (40° C.), and then the gas in the autoclave was evacuated, and the pressure in the vessel was adjusted to the atmospheric pressure by introducing air into the autoclave. After that, the atmospheric gas in the autoclave was replaced twice with nitrogen, and the reaction solution was collected from the vessel in the autoclave, and introduced into a recovery flask. After that, the vessel in the autoclave was washed with chloroform and water. The liquid (washing liquid) used for the washing was also collected, and added to the recovery flask to which the reaction solution was introduced. Thus, a solution containing the reaction product was obtained in the recovery flask.

Next, methanol was evaporated from the solution (solution containing the reaction product) by using a rotary evaporator, and then 20 mL of chloroform and 20 mL of water were added to the obtained residue to dissolve the residue and obtain a mixture liquid. Subsequently, the mixture liquid was transferred to a separatory funnel, and shaken well. Then, the chloroform layer was collected to obtain a chloroform solution. Subsequently, the chloroform solution was washed once with 20 mL of 5% by mass dilute hydrochloric acid, and then further once with 20 mL of water saturated aqueous sodium hydrogen carbonate. Next, the washed chloroform solution was dried by adding anhydrous sodium sulfate for removal of water, followed by filtration. The obtained filtrate was concentrated to obtain a product (white solid) (Yield: 0.95 g, Percentage yield: 770).

Figure 2:
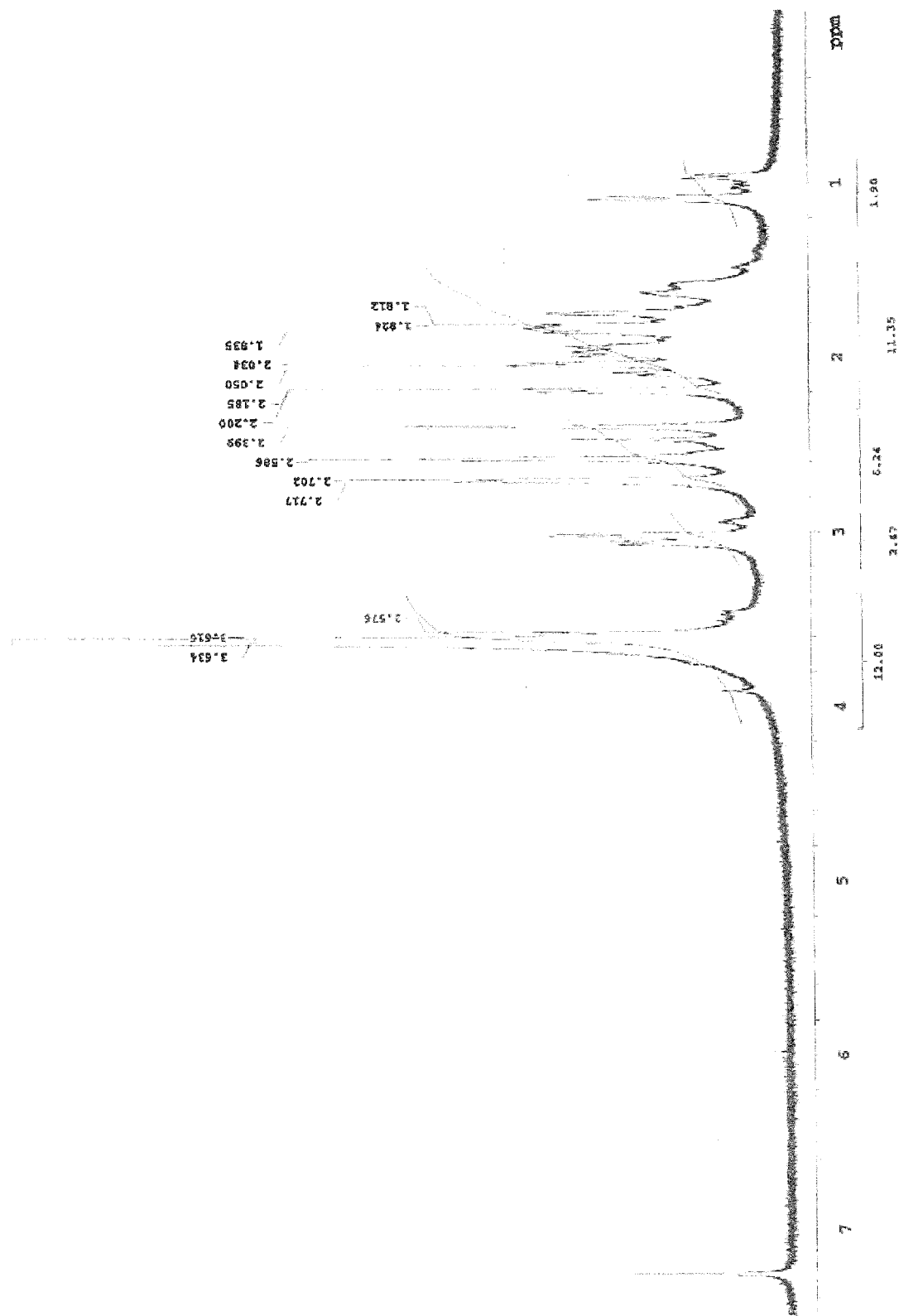
FIG. 2 is a graph showing a $^1$H-NMR (CDCl$_3$) spectrum of the compound obtained in Example 1.
Figure 3:
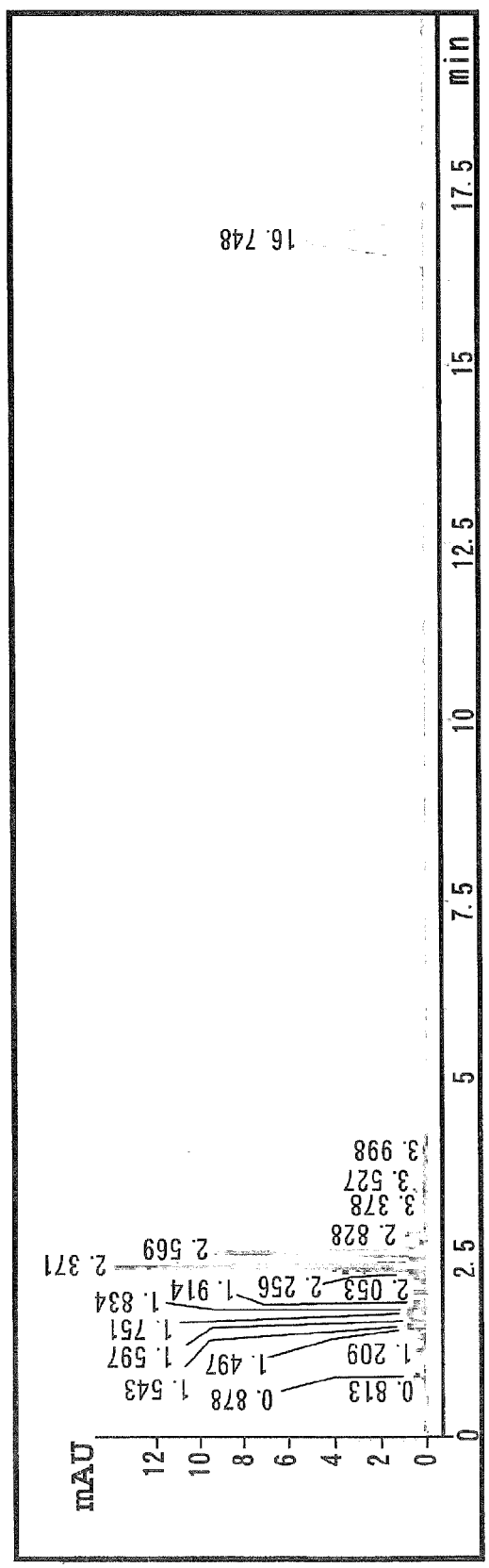
FIG. 3 is a graph showing a spectrum obtained by subjecting the compound obtained in Example 1 to HPLC measurement (for which an UV detector was used, and the absorption wavelength was set to 210.8 nm).
Figure 4:
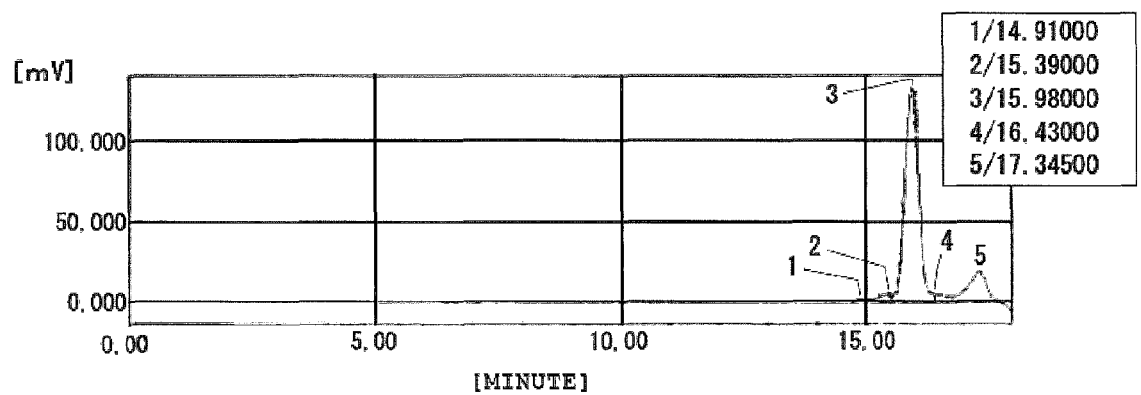
FIG. 4 is a graph showing a spectrum obtained by subjecting the compound obtained in Example 1 to GPC measurement.

To identify compounds in the thus obtained product, $^1$H-NMR measurement, IR measurement, HPLC measurement, and GPC measurement were carried out. Note that, for the NMR measurement, a measuring apparatus INOVA-600 manufactured by VARIAN Inc. was used. Meanwhile, for the IR measurement, a measuring apparatus JASCO FT/IR-4100 manufactured by JASCO Corporation was used. For the HPLC measurement, a detector 1200 series manufactured by Agilent was used as a measuring apparatus, a mixture solvent in which the ratio of acetonitrile to water was 70:30 in terms of the mole ratio ([acetonitrile]:[water]) was used as the eluent, and a column manufactured by Agilent under the product name of "SB-C18" was used. In addition, for the GPC measurement, a measuring apparatus manufactured by Tosoh Corporation under the product name of "HLC8200-GPC" was used, and tetrahydrofuran was used as the eluent. Regarding the results of these measurements, FIG. 1 shows a graph showing an IR spectrum of the compound obtained in Example 1; FIG. 2 shows a graph showing a $^1$H-NMR (CDCl$_3$) spectrum of the compound obtained in Example 1; FIG. 3 shows a graph showing a spectrum obtained by subjecting the compound obtained in Example 1 to the HPLC measurement (for which an UV detector was used as the detector, and the absorption wavelength thereof was set to 210.8 nm); and FIG. 4 shows a graph showing a spectrum obtained by subjecting the compound obtained in Example 1 to GPC measurement.

From these results of the measurements, it was found that a norbornane tetracarboxylic acid tetramethyl ester (target product) represented by the following general formula (28) was formed:

[Chem. 8]

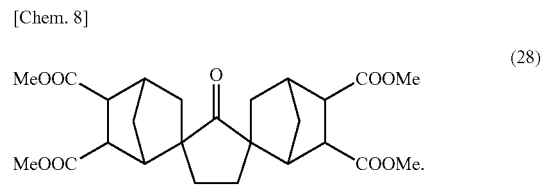

(28)

In addition, from the result (area ratio) of the GPC measurement, it was found that the content ratio of a polymerization product formed by the ring-opening polymerization of the norbornene ring in the norbornene compound represented by the above-described general formula (16) (hereinafter, simply referred to as "polymerization product" in some cases) was 2.9% by mole in the product. In addition, from the results of the HPLC measurement, it was found that the rest of the product other than the polymerization product was only the norbornane tetracarboxylic acid tetramethyl ester represented by the above-described general formula (28), and no intermediate in which the esterification proceeded only on one side of the norbornene compound represented by the above-described general formula (16) (norbornane dicarboxylic acid dimethyl ester represented by the following general formula (29)

[Chem. 9]

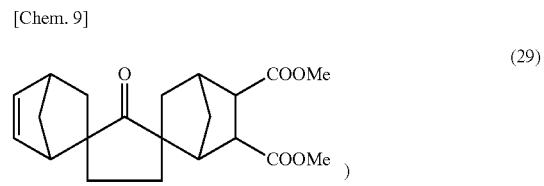

(29)

was formed, and that no norbornene compound represented by the above-described general formula (16) (raw material compound) remained. Accordingly, the selectivity for the norbornane tetracarboxylic acid tetramethyl ester was found to be 97.1%.

Note that Table 1 shows the selectivity for the norbornane tetracarboxylic acid tetramethyl ester (target product) represented by the above-described general formula (28), the selectivity for the norbornane dicarboxylic acid dimethyl ester (intermediate: by-product) represented by the above-described general formula (29) (the ratio (by mole) of the raw material compound converted to the intermediate after the reaction), the selectivity for the polymerization product (by-product) formed by the ring-opening polymerization of the norbornene compound represented by the above-described general formula (16) (the ratio (by mole) of the raw material compound converted to the polymerization product after the reaction), and the ratio (by mole) of the remaining norbornene compound represented by the above-described general formula (16).

Example 2

A product (white solid) was obtained in the same manner as in Example 1, except that the amount of copper acetate monohydrate used was changed from 25.7 mg to 51.4 mg, and that the amount of manganese acetate tetrahydrate used was changed from 121.2 mg to 30.3 mg (Yield: 0.95 g, Percentage yield: 77%).

To identify the kinds of compounds in the thus obtained product and the structures thereof, HPLC measurement and GPC measurement were conducted in the same manner as in Example 1. The results of these measurements showed that the norbornane tetracarboxylic acid tetramethyl ester represented by the above-described general formula (28) was formed. Note that, from the result (area ratio) of the GPC measurement, it was found that the content ratio of the polymerization product formed by the ring-opening polymerization of the norbornene ring in the norbornene compound represented by the above-described general formula (16) was 7.6% by mole in the product. Moreover, Table 1 shows the selectivity for the norbornane tetracarboxylic acid tetramethyl ester (target product) represented by the above-described general formula (28), the selectivity for the norbornane dicarboxylic acid dimethyl ester (intermediate: by-product) represented by the above-described general formula (29), the selectivity for the polymerization product (by-product) formed by the ring-opening polymerization of the norbornene compound represented by the above-described general formula (16), and the ratio (by mole) of the remaining norbornene compound represented by the above-described general formula (16), which were determined from the results of the measurements.

Example 3

A product (white solid) was obtained in the same manner as in Example 1, except that the amount of manganese acetate tetrahydrate used was changed from 121.2 mg to 60.6 mg (Yield: 1.05 g, Percentage yield: 85.4%).

To identify the kinds of compounds in the thus obtained product and the structures thereof, HPLC measurement and GPC measurement were conducted in the same manner as in Example 1. The results of these measurements showed that the norbornane tetracarboxylic acid tetramethyl ester represented by the above-described general formula (28) was formed. In addition, Table 1 shows the selectivity for the norbornane tetracarboxylic acid tetramethyl ester (target product) represented by the above-described general formula (28), the selectivity for the norbornane dicarboxylic acid dimethyl ester (intermediate: by-product) represented by the above-described general formula (29), the selectivity for the polymerization product (by-product) formed by the ring-opening polymerization of the norbornene compound represented by the above-described general formula (16), and the ratio (by mole) of the remaining norbornene compound represented by the above-described general formula (16), which were determined from the results of the measurements. Note that, from the result (area ratio) of the GPC measurement, it was found that the content ratio of the polymerization product formed by the ring-opening polymerization of the norbornene ring in the norbornene compound represented by the above-described general formula (16) was 6.2% by mole in the product.

Example 4

A product (white solid) was obtained in the same manner as in Example 1, except that the amount of manganese acetate tetrahydrate used was changed from 121.2 mg to 90.9 mg (Yield: 0.98 g, Percentage yield: 80%).

To identify the kinds of compounds in the thus obtained product and the structures thereof, HPLC measurement and GPC measurement were conducted in the same manner as in Example 1. The results of these measurements showed that the norbornane tetracarboxylic acid tetramethyl ester represented by the above-described general formula (28) was formed. In addition, Table 1 shows the selectivity for the norbornane tetracarboxylic acid tetramethyl ester (target product) represented by the above-described general formula (28), the selectivity for the norbornane dicarboxylic acid dimethyl ester (intermediate: by-product) represented by the above-described general formula (29), the selectivity for the polymerization product (by-product) formed by the ring-opening polymerization of the norbornene compound represented by the above-described general formula (16), and the ratio (by mole) of the remaining norbornene compound represented by the above-described general formula (16), which were determined from the results of the measurements. Note that, from the result (area ratio) of the GPC measurement, it was found that the content ratio of the polymerization product formed by the ring-opening polymerization of the norbornene ring in the norbornene compound represented by the above-described general formula (16) was 3.0% by mole in the product.

Example 5

A product (white solid) was obtained in the same manner as in Example 1, except that the amount of manganese acetate tetrahydrate used was changed from 121.2 mg to 30.3 mg (Yield: 0.98 g, Percentage yield: 80%).

To identify the kinds of compounds in the thus obtained product and the structures thereof, HPLC measurement and GPC measurement were conducted in the same manner as in Example 1. The results of these measurements showed that the norbornane tetracarboxylic acid tetramethyl ester represented by the above-described general formula (28) was formed. In addition, Table 1 shows the selectivity for the norbornane tetracarboxylic acid tetramethyl ester (target product) represented by the above-described general formula (28), the selectivity for the norbornane dicarboxylic acid dimethyl ester (intermediate: by-product) represented by the above-described general formula (29), the selectivity for the polymerization product (by-product) formed by the ring-opening polymerization of the norbornene compound represented by the above-described general formula (16), and the ratio (by mole) of the remaining norbornene compound represented by the above-described general formula (16), which were determined from the results of the measurements. Note that, from the result (area ratio) of the GPC measurement, it was found that the content ratio of the polymerization product formed by the ring-opening polymerization of the norbornene ring in the norbornene compound represented by the above-described general formula (16) was 7.0% by mole in the product.

Comparative Example 1

A product (white solid) was obtained in the same manner as in Example 5, except that a Pd(OAc)$_2$ solution obtained amount of copper acetate to the mole amount of the raw material compound, the ratio (([manganese chloride]/[raw material compound])×100) of the mole amount of manganese chloride to the mole amount of the raw material compound, and the ratio (([manganese acetate]/[raw material compound])×100) of the mole amount of manganese acetate to the mole amount of the raw material compound.

TABLE 1

| | Type of palladium catalyst | Raw material compound (mmol) | Palladium catalyst | Mole ratio to amount of moles of raw material compound | | | Reaction products | | | |
| | | | | Copper acetate (Cu(OAc)$_2$) | Manganese chloride (MnCl$_2$) | Manganese acetate (Mn(OAc)$_2$) | Selectivity for target product (%) | Selectivity for polymerization product (%) | Selectivity for intermediate (%) | Ratio of remaining raw material compound (%) |
|---|---|---|---|---|---|---|---|---|---|---|
| Example 1 | Pd(bpy)Cl$_2$ | 2.58 | 0.01 | 5.0 | 3.8 | 19.2 | 97.1 | 2.9 | 0 | 0 |
| Example 2 | Pd(bpy)Cl$_2$ | 2.58 | 0.01 | 10.0 | 3.8 | 4.8 | 92.4 | 7.6 | 0 | 0 |
| Example 3 | Pd(bpy)Cl$_2$ | 2.58 | 0.01 | 5.0 | 3.8 | 9.6 | 93.8 | 6.2 | 0 | 0 |
| Example 4 | Pd(bpy)Cl$_2$ | 2.58 | 0.01 | 5.0 | 3.8 | 14.4 | 97.0 | 3.0 | 0 | 0 |
| Example 5 | Pd(bpy)Cl$_2$ | 2.58 | 0.01 | 5.0 | 3.8 | 4.8 | 93.0 | 7.0 | 0 | 0 |
| Comparative Example 1 | Pd(OAc)$_2$ | 2.58 | 0.01 | 5.0 | 3.8 | 4.8 | 91.5 | 8.5 | 0 | 0 | by dissolving 4.63 mg of palladium acetate (Pd(OAc)$_2$) in 80 mL of a methanol solution was prepared instead of the Pd(bpy)Cl$_2$ solution, and 1.0 mL of the Pd(OAc)$_2$ solution was used instead of 1.0 mL of the Pd(bpy)Cl$_2$ solution (Yield: 0.95 g, Percentage yield: 77%). In this manner, the product was obtained by the same procedure as in Example 1, except that the type of the palladium catalyst was changed from Pd(bpy)Cl$_2$ to Pd(OAc)$_2$.

To identify the kinds of compounds in the thus obtained product and the structures thereof, HPLC measurement and GPC measurement were conducted in the same manner as in Example 1. The results of these measurements showed that the norbornane tetracarboxylic acid tetramethyl ester represented by the above-described general formula (28) was formed. In addition, Table 1 shows the selectivity for the norbornane tetracarboxylic acid tetramethyl ester (target product) represented by the above-described general formula (28), the selectivity for the norbornane dicarboxylic acid dimethyl ester (intermediate: by-product) represented by the above-described general formula (29), the selectivity for the polymerization product (by-product) formed by the ring-opening polymerization of the norbornene compound represented by the above-described general formula (16), and the ratio (by mole) of the remaining norbornene compound represented by the above-described general formula (16), which were determined from the results of the measurements. Note that, from the result (area ratio) of the GPC measurement, it was found that the content ratio of the polymerization product formed by the ring-opening polymerization of the norbornene ring in the norbornene compound represented by the above-described general formula (16) was 8.5% by mole in the product.

Note that, regarding each of Examples 1 to 5 and Comparative Example 1, Table 1 shows the ratio (([palladium catalyst]/[raw material compound])×100) of the mole amount of the palladium catalyst (Examples 1 to 5: Pd(bpy)Cl$_2$, Comparative Example 1: Pd(OAC)$_2$) to the mole amount of the raw material compound, the ratio (([copper acetate]/[raw material compound])×100) of the mole As is apparent from the results shown in Table 1, not only the selectivity for the target product was sufficiently high, but also the intermediate (reaction intermediate) was not formed (did not remain) and the raw material compound did not remain, in each of the cases (Examples 1 to 5) where the palladium complex having a bipyridyl as a ligand (Pd(bpy)Cl$_2$) was used as a catalyst. Moreover, the selectivity for the polymerization product (the ratio of the raw material compound converted to the polymerization product after the reaction) was 7.6% or lower. Accordingly, it was found that the formation of the by-products such as the polymerization product was sufficiently suppressed. In addition, from the results of the products obtained in Examples 1 and 3 to 5, it was found that when the palladium complex having a bipyridyl as a ligand (Pd(bpy)Cl$_2$) was used as the catalyst, the selectivity was more improved and the formation of the polymerization product was more suppressed with the increase in the amount of manganese acetate tetrahydrate used. In contrast, in the case (Comparative Example 1) where the catalyst other than the palladium complex having a bipyridyl as a ligand (Pd(bpy)Cl$_2$) was used, the ratio of the polymerization product formed was 8.5% by mole.

From these results, it was found that the selectivity for the target product was higher in the case where the palladium complex having a bipyridyl as a ligand (Pd(bpy)Cl$_2$) was used as the catalyst as described in each of Examples 1 to 5 than in the case (Comparative Example 1) where Pd(OAc)2 was used as the catalyst. In addition, a comparison of Example 5 and Comparative Example 1 between which the same conditions were employed, except that the type of the palladium catalyst was changed showed that, by using the palladium complex having a bipyridyl as a ligand (Pd(bpy)Cl$_2$), it is possible to reduce the selectivity for the polymerization product (the ratio of the raw material compound converted to the polymerization product in the reaction to the raw material compound consumed in the reaction) by as much as 1.5%. From these results, it has been found that the present invention makes it possible to produce the target ester compound with a sufficiently advanced level of selectivity, while suppressing the formation of the by-products at a further advanced level.

Note that the present inventors have found that, when, for example, the product was used as a raw material of a polyimide, the polymerization product as a by-product constitutes a factor which may cause problems such as color development in the polyimide. For this reason, considering the industrial production of polyimide and the like, the present inventors believe that it is highly necessary to reduce the amount of the polymerization product formed at a further advanced level. From such a viewpoint, the method for producing an ester compound of the present invention (Examples 1 to 5), which is a method making it possible to sufficiently suppress the formation of the by-products at a further advanced level, and moreover making it possible to efficiently produce the ester compound with a sufficiently high selectivity, can be particularly suitably used as a method for preparing a monomer used for producing a polyimide with sufficiently high qualities.

INDUSTRIAL APPLICABILITY

As described above, according to the present invention, it is possible to provide a method for producing an ester compound by which the formation of the by-products can be sufficiently suppressed, and by which the ester compound can be efficiently produced with a sufficiently high selectivity.

Accordingly, the method for producing an ester compound of the present invention, which makes it possible to produce an ester compound with a sufficiently advanced level of selectivity, is especially useful as a method for industrially producing an ester compound which can be used for various applications (for example, as a monomer of a polyimide and the like), etc.

The invention claimed is:

1. A method for producing an ester compound, comprising:
reacting a compound having at least one cyclic structure selected from the group consisting of a norbornene ring and a norbornadiene ring with an alcohol and carbon monoxide in the presence of a palladium catalyst and an oxidizing agent, to thereby introduce ester groups to carbon atoms forming a double bond in the cyclic structure and obtain the ester compound, wherein
the palladium catalyst comprises a palladium complex having a bipyridyl as a ligand.

2. The method for producing an ester compound according to claim 1, wherein
oxygen is used as the oxidizing agent.

3. The method for producing an ester compound according to claim 2, wherein
a chlorine-containing compound, a copper compound other than a chloride, and a manganese compound other than a chloride are used in combination with the oxidizing agent.

4. The method for producing an ester compound according to claim 2, wherein manganese chloride, copper acetate, and manganese acetate are used in combination with the oxidizing agent.

5. The method for producing an ester compound according to claim 1, wherein
the palladium complex having a bipyridyl as a ligand is a palladium complex represented by $Pd(bpy)X_2$, wherein bpy represents the bipyridyl, and X represents a monovalent anionic ligand selected from the group consisting of a halogen ligand, an acetate ligand, an acetylacetone ligand, an alkyl ligand, a nitrile ligand, a hydride ligand, an aryl ligand, and an allyl ligand.

6. The method for producing an ester compound according to claim 5, wherein
X is chlorine.

7. The method for producing an ester compound according to claim 1, wherein
the compound having at least one cyclic structure selected from the grou consisting of a norbornene ring and a norbornadiene ring is selected from the grou consisting of:

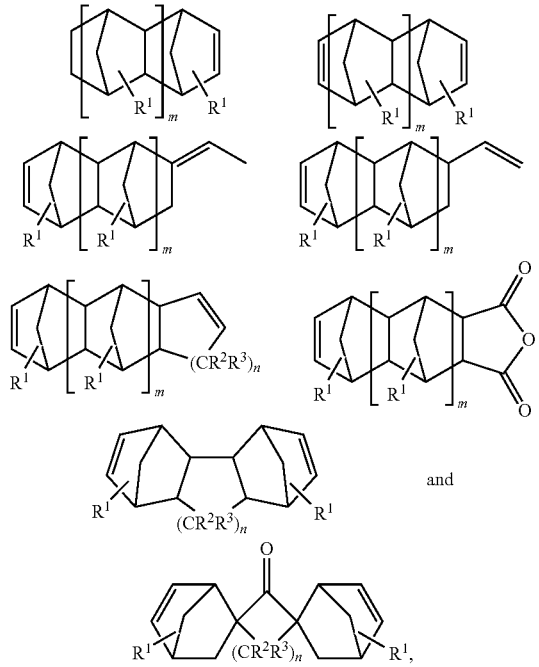

and wherein $R^1$, $R^2$, and $R^3$ each independently represent one selected from the group consisting of a hydrogen atom, alkyl groups having 1 to 10 carbon atoms, and a fluorine atom, n represents an integer of 0 to 12, and m represents an integer of 0 to 5.

* * * * *